(12) United States Patent
Chiou

(10) Patent No.: US 10,765,611 B2
(45) Date of Patent: Sep. 8, 2020

(54) WATER-BASED COSMETIC COMPOSITION COMPRISING AN EFFECT PIGMENT AND A COSMETIC ACTIVE

(71) Applicant: L'OREAL, Paris (FR)

(72) Inventor: Catherine Chiou, Saddle Brook, NJ (US)

(73) Assignee: L'Oreal, Paris (FR)

( * ) Notice: Subject to any disclaimer, the term of this patent is extended or adjusted under 35 U.S.C. 154(b) by 52 days.

(21) Appl. No.: 15/786,792

(22) Filed: Oct. 18, 2017

(65) Prior Publication Data
US 2019/0110967 A1    Apr. 18, 2019

(51) Int. Cl.
| | |
|---|---|
| *A61K 8/34* | (2006.01) |
| *A61K 8/25* | (2006.01) |
| *A61K 8/92* | (2006.01) |
| *A61K 8/67* | (2006.01) |
| *A61Q 1/02* | (2006.01) |
| *A61K 8/73* | (2006.01) |
| *A61K 8/86* | (2006.01) |
| *A61K 8/39* | (2006.01) |
| *A61K 8/63* | (2006.01) |
| *A61K 8/60* | (2006.01) |
| *A61Q 19/08* | (2006.01) |
| *A61Q 19/00* | (2006.01) |

(52) U.S. Cl.
CPC ............... *A61K 8/345* (2013.01); *A61K 8/25* (2013.01); *A61K 8/39* (2013.01); *A61K 8/60* (2013.01); *A61K 8/63* (2013.01); *A61K 8/676* (2013.01); *A61K 8/678* (2013.01); *A61K 8/73* (2013.01); *A61K 8/737* (2013.01); *A61K 8/86* (2013.01); *A61K 8/922* (2013.01); *A61Q 1/02* (2013.01); *A61K 2800/43* (2013.01); *A61K 2800/48* (2013.01); *A61Q 19/007* (2013.01); *A61Q 19/08* (2013.01)

(58) Field of Classification Search
CPC ... A61Q 1/02; A61K 8/60; A61K 8/63; A61K 8/39; A61K 8/767; A61K 8/73; A61K 8/86; A61K 8/737; A61K 8/678; A61K 8/922; A61K 8/25; A61K 8/345
See application file for complete search history.

(56) References Cited

U.S. PATENT DOCUMENTS

| | | | |
|---|---|---|---|
| 7,049,300 B2 | 5/2006 | Dalko et al. | |
| 8,221,536 B2 | 7/2012 | Hollman et al. | |
| 2008/0008674 A1 | 1/2008 | Burnier et al. | |
| 2008/0152604 A1* | 6/2008 | Doering | A61K 8/362 424/60 |
| 2008/0241084 A1* | 10/2008 | Siddiqui | A61K 8/97 424/62 |
| 2012/0039830 A1* | 2/2012 | Kurahashi | A61K 8/4993 424/63 |
| 2014/0112877 A1* | 4/2014 | Niki | A61Q 19/02 424/62 |

FOREIGN PATENT DOCUMENTS

CN      107137327    *   9/2017

OTHER PUBLICATIONS

Shuli, CN 107137327, published: Sep. 8, 2017, English machine translation obtained on Jun. 11, 2018.*

* cited by examiner

*Primary Examiner* — Juliet C Switzer
*Assistant Examiner* — Genevieve S Alley
(74) *Attorney, Agent, or Firm* — McNees, Wallace & Nurick LLC

(57) ABSTRACT

The disclosure relates to an aqueous cosmetic composition that includes at least one effect pigment is present up to about 0.02 wt %, an emulsion of at least one oil and at least one surfactant, and at least one active selected to provide one or more benefits, including, but not limited to brightening/whitening, improvement of skin tone, blemish control or reduction, reduction of redness, anti-aging, and hydration, in an aqueous solvent. The composition may include a thickener and a preservative. Methods include forming the composition and applying the composition to the skin to provide an instant "glowing" or "brightening" effect.

26 Claims, No Drawings

WATER-BASED COSMETIC COMPOSITION COMPRISING AN EFFECT PIGMENT AND A COSMETIC ACTIVE

FIELD OF THE INVENTION

The present disclosure relates to a cosmetic composition a water-based liquid cosmetic composition comprising one or more effect pigments and a water-based toner, to provide an instant "glowing" or "brightening" effect on keratinous tissue.

BACKGROUND OF THE INVENTION

Cosmetic compositions that provide an immediate visual effect include relatively large amounts of effect pigments, typically on the order of from about 0.5% to about 1%, by weight, based on the weight of the composition, for facial creams. And the amount of effect pigments is even greater in makeup products, such as foundation, blusher, eye shadow, eye pencil, and mascara, typically on the order of from about 5% to about 10%, by weight, based on the weight of the composition. Such compositions are provided as water in oil type emulsions, and typically include at least humectants as actives, along with relatively large quantities of oils, emulsifiers, and thickeners. While such compositions are selected by consumers for their aesthetic properties, they tend to be heavy on the skin, and they confer an obvious and intense makeup effect that is not appealing to many consumers, particularly those consumers with a younger demographic.

Accordingly, there is a need in the art for a light, water-based cosmetic composition that confers a short or long-term skin benefit and provides a light and bright immediate effect that is less made up and not weighty. Thus, the objective for the invention according to the instant disclosure is to provide a water-based liquid cosmetic composition comprising effect pigment in a water-based toner comprising at least one active to provide an instant "glowing" or "brightening" effect on keratinous tissue.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In an exemplary embodiment, an aqueous cosmetic composition comprises at least one effect pigment that is present in an amount of up to about 0.02% by weight, based on the total weight of the composition (wt %), an emulsion comprising at least one oil and at least one surfactant, at least one active, and a solvent comprising water. In some embodiments, the composition comprises one or more of a least one thickener or thickening agent and at least one preservative.

In another exemplary embodiment, an aqueous cosmetic composition comprises from about 0.001 to about 0.02 wt % of an effect pigment; an emulsion of an oil and a surfactant, the emulsion comprising from about 0.1 to about 1.0 wt % of at least one surfactant and from about 0.01 to about 0.2 wt % of an oil; from about 0.0001 to 15 wt % of an active; and up to about 99 wt % of water. In some particular embodiments, the effect pigment comprises a synthetic fluorphlogopite (and) titanium dioxide.

A further aspect of the invention provides a method for preparing an aqueous cosmetic composition, the method comprising: a. providing from about 0.001 to 0.02 wt % of an effect pigment; b. providing an emulsion of an oil and a surfactant, the emulsion comprising from about 0.1 to 1.0 wt % of at least one surfactant and from about 0.01 to about 0.2 wt % of an oil; c. providing from about 0.0001 to 15 wt % of an active; and d. providing up to about 99 wt % of water; e. mixing the components a.-d.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

"Keratinous tissue," as used herein, includes, but is not limited to, skin, hair, and nails.

The term "lasting," as used in connection with the effect conferred by the effect pigment, is meant to convey that the immediate visual effect conferred by the effect pigment is substantially intact on the skin and lasts for at least about 2 hours to about 12 hours, to about 24 hours after application of the composition to keratinous tissue, particularly to skin.

The disclosure relates to an aqueous composition and methods for improving the appearance of the skin. The disclosure provides a skin toner composition that confers an instant glowing or brightening iridescent effect and that comprises one or more actives directed to skin brightening, blemish treatment, skin tone, anti-aging and hydration in a water-based solvent.

According to the various embodiments, the effect pigment is dosed at an extremely low concentration in the composition to give a unique optical effect on keratinous tissue without having the appearance of "makeup" product. Applicants have surprisingly discovered that inclusion of the effect pigment in a water-based toner can provide a lasting glowing or brightening iridescent effect at effect pigment levels that are not more than 0.02 wt %.

In accordance with the various embodiments, an aqueous cosmetic composition comprises at least one effect pigment that is present in an amount of up to about 0.02 wt %, an emulsion comprising at least one oil and at least one surfactant, at least one active selected to provide one or more benefits, including, but not limited to brightening/whitening, improvement of skin tone, blemish control or reduction, reduction of redness, anti-aging, and hydration, and a solvent comprising water. In some embodiments, the composition comprises one or more of a least one thickener or thickening agent and at least one preservative.

In another exemplary embodiment, an aqueous cosmetic composition comprises from about 0.001 to about 0.02 wt % of an effect pigment; an emulsion of an oil and a surfactant, the emulsion comprising from about 0.1 to about 1.0 wt % of at least one surfactant and from about 0.01 to about 0.2 wt % of an oil; from about 0.0001 to 15 wt % of an active; and up to about 99 wt % of water. In some particular embodiments, the effect pigment comprises a synthetic fluorphlogopite (and) titanium dioxide.

In another exemplary embodiment, a method of preparing an aqueous cosmetic composition includes a. providing from about 0.001 to 0.02 wt % of an effect pigment; b. providing an emulsion of an oil and a surfactant, the emulsion comprising from about 0.1 to 1.0 wt % of at least one surfactant and from about 0.01 to about 0.2 wt % of an oil; c. providing from about 0.0001 to 15 wt % of an active; and d. providing up to about 99 wt % of water; e. mixing the components a.-d.

Compositions

Effect Pigment

In accordance with the various embodiments, one or more effect pigments are present in the composition. By way of non-limiting example, effect pigments may be chosen from synthetic fluorphlogopite based, multilayered pigments, including "optically variable pigments" to provide a striking pearlescent effect. Including mica and borosilicate.

In at least certain embodiments, the at least one effect pigment may be chosen from synthetic fluorphlogopite pigments that comprise a metal oxide, such as but not limited to titanium dioxide and iron oxide. And in some particular embodiments, the effect pigment comprises at least one synthetic fluorphlogopite and a metal oxide. Reference may be made to U.S. Pat. No. 8,221,536 which discloses examples of synthetic fluorphlogopite and prophetic examples of cosmetics that include from 1 to more than 15 wt % synthetic fluorphlogopite. In some exemplary embodiments described herein, the synthetic fluorphlogopite is obtained from SunChemical, from the line of SUNSHINE SPECTRAL EFFECTS. The pigments are generally characterized by percentage content of synthetic fluorphlogopite and metal oxide and particle size, wherein the percent oxide ranges from 35-85 wt % and the percent pigment ranges from 15-65 wt %, and the particle size that ranges from about 10 micrometers to about 75 micrometers, from about 20 micrometers to about 60 micrometers, from about 30 micrometers to about 50 micrometers, and from about 10 micrometers to about 15 micrometers.

In accordance with the various embodiments, one or more effect pigments are present in the composition in an amount from about 0.001 to about 0.2 wt %, from about 0.001 to about 0.1 wt %, from about 0.001 to about 0.02 wt %, from about 0.0025 to about 0.015 wt %, from 0.005 to about 0.0125 wt %, and from 0.0075 to about 0.01 wt %. In some embodiments, the composition comprises two or more effect pigments, the combination of which is present in an amount from about 0.001 to about 0.04 wt %, from about 0.001 to about 0.02 wt %, from about 0.0025 to about 0.015 wt %, from 0.005 to about 0.0125 wt %, and from 0.0075 to about 0.01 wt %. In some embodiments, the one or more effect pigments are present in the composition in an amount that is not more than 0.02 wt %, or not more than about 0.01 wt %.

Thus, each one or a combination of effect pigments may be present by weight, based on the total weight of the composition, from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19 to about 0.2 percent, including increments and ranges therein and there between.

Emulsion Comprising Oil and Surfactant

Surfactant

In accordance with the various embodiments, the composition comprises an emulsion that comprises one or more surfactants, alone or in combination, with at least one oil (as described below).

In accordance with the disclosure, by way of non-limiting example, the at least one surfactant in the emulsion may be chosen from alkoxylated alcohol, for example, PPG-6-Decyltetradeceth-30, PPG-26-BUTETH-26, CETETH-20, STEARETH-20 and combinations thereof.

The at least one surfactant in the emulsion may be present in an amount ranging from about 0.1 to about 5 wt %, for example from about 0.1 to about 1 wt %, from about 0.1 to about 0.5 wt %, or from about 0.1 to about 0.2 wt %. In at least certain exemplary embodiments, the surfactant is present in an amount less than about 1 wt %, such as less than about 0.5 wt %. In some other embodiments, the at least one surfactant is present in an amount up to about 5 wt %.

Thus, the one or combination of surfactants in the emulsion may be present by weight, based on the total weight of the composition, from about 0.1, 0.2, 0.3, 0.4, 0.5, 0.6, 0.7, 0.8, 0.9, 1.0, 2, 3, 4, to about 5 percent, including increments and ranges therein and there between.

Oil

In accordance with the various embodiments, the composition comprises an emulsion that comprises one or more oils, alone or in combination, with at least one surfactant (as described above).

In accordance with the disclosure, by way of non-limiting example, the at least one oil in the emulsion may be chosen from botanical and essential oils, such as *Lavandula angustifolia* (lavender) oil, *pelargonium graveolens* flower oil, *citrus aurantium* dulcis (orange) peel oil, *Rosmarinus officinalis* (rosemary) leaf oil, *menthe viridis* (spearmint) leaf oil, *citrus aurantifolia* (lime) oil, *melaleuca alternifolia* (tea tree) leaf oil, *citrus grandis* (grapefruit) peel oil, *citrus medica* limonum (lemon) peel oil, rose flower oil, *eucalyptus globulus* leaf oil, and combinations thereof.

The at least one oil in the emulsion may be present in the composition from about 0.01 to about 1 wt %, for example from about 0.01 to about 0.5 wt %, from about 0.01 to about 0.3 wt %, or from about 0.01 to about 0.2 wt %. In at least certain exemplary embodiments, the oil is present in an amount less than about 0.5 wt %, such as less than about 0.3 wt %. In some other embodiments, the at least one oil is present in an amount up to about 1 wt %.

Thus, the one or combination of oil in the emulsion may be present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, to about 1.0 percent, including increments and ranges therein and there between.

Actives

In accordance with the various embodiments, the composition comprises at least one active, and in some embodiments, more than one active. In some embodiments, there may be one or more actives present in the cosmetic composition, according to the disclosure, the active selected to provide one or more benefits, including, but not limited to brightening/whitening, improvement of skin tone, blemish control or reduction, reduction of redness, anti-aging, and hydration.

In some embodiments, the actives may be selected from anti-aging compositions including retinol, retinol derivatives, *anogeissus leiocarpus* bark extract, hydrolyzed rhodophycea extract, hydrolyzed linseed extract, pseudoalteromonas ferment extract, *manilkara multinervis* leaf Extract, *Lavandula hybrida* oil, *grifola frondosa* fruiting body extract, *plantago lanceolata* leaf extract, *cyathea medullaris* leaf extract, hydrolyzed hyaluronic acid, *malus domestica* fruit cell culture extract, resveratrol, salicyloyl phytosphingosine and combinations thereof.

In some embodiments, the actives may be selected from oily skin treatment compositions including lens *esculenta* (lentil) seed extract, sarcosine, *peumus boldus* leaf extract,

*crithmum maritimum* extract, niacinamide, salicylic acid, hydroxyethylpiperazine ethane sulfonic acid, *spiraea ulmaria* extract, pentaerythrityl tetra-di-t-butyl hydrox yhydrocinnamate and combinations thereof.

In some embodiments, the actives may be selected from skin tone improving compositions including hydrolyzed rice protein, *ophiopogon japonicus* root extract, *chenopodium quinoa* seed extract, tamarindus indica seed gum, xylitylglucoside (and) anhydroxylitol (and) xylitol, ceramide derivatives, *Helianthus annuus* (sunflower) seed oil unsaponifiables, myristyl malate phosphonic acid, mannose, 2-oleamido-1,3-oct adec anedi and combinations thereof.

In some embodiments, the actives may be selected from anti-redness compositions including madecassoside, saccharide isomerate, palmitoyl tripeptide-8, panthenol, *Olea europaea* (olive) leaf extract, *Mentha piperita* (peppermint) extract, *leontopodium alpinum* extract, dipotassium glycyrrhizate, acetyl dipeptide-1 cetyl ester, acetyl tetrapeptide-15, boswellia serrata extract, sodium palmitoyl proline (and) *nymphaea alba* flower extract and combinations thereof.

In some embodiments, the actives may be selected from glycerin and glycols such as, for example, propylene glycol, butylene glycol, dipropylene glycol and diethylene glycol, glycol ethers such as monopropylene, dipropylene and tripropylene glycol alkyl($C_1$-$C_4$) ethers, monoethylene, diethylene and triethylene glycol; salicylic acid and combinations thereof.

In some embodiments, the actives may be selected from extracts of algae and of planktons, enzymes and coenzymes, ceramides, anti-oxidant compounds, including, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin, pine bark, and other extracts and combinations thereof.

In some embodiments, the actives may be selected from anti-elastase and anti-collagenase agents, peptides, fatty acid derivatives, steroids; free-radical scavengers, vitamins and vitamin derivatives, such as ascorbic acid, and Vitamin E.

In some embodiments, the actives may be selected from sunscreen agents (e.g., inorganic sunscreen agent, such as titanium dioxide and zinc oxide and organic sunscreen agents, such as octocrylene, ethylhexyl salicylate, homosalate, and avobenzone); and combinations thereof.

In some particular embodiments, at least one active is water soluble.

In some exemplary embodiments, the composition comprises at least one anti-aging composition, such as hydroxypropyl tetrahydropyrantriol, at least one humectant, such as methyl gluceth-20, and at least one vitamin or vitamin derivative, such as one of sodium citrate, citric acid, dipotassium glycyrrhizate, 3-O-ethyl ascorbic acid, and tocopherol and combinations thereof.

In some particular embodiments, the at least one active may be chosen from glycerin, glycol, methyl gluceth-20, hydroxypropyl tetrahydropyrantriol, tocopherol, sodium citrate, citric acid, 3-O-ethyl ascorbic acid, and plant extracts, *Paeonia Suffruticosa* Root Extract, and *Citrus Aurantium* Tachibana Peel Extract and combinations thereof. Optionally, combinations of actives may be present in the compositions according to the disclosure. For example, an exemplary composition may include two or more actives. And in some exemplary compositions the actives glycerin, dipropylene glycol, methyl gluceth-20, hydroxypropyl tetrahydropyrantriol, tocopherol, sodium citrate, citric acid, dipotassium glycyrrhizate, 3-O-ethyl ascorbic acid, and plant extracts, *Paeonia Suffruticosa* Root Extract, *Citrus Aurantium* Tachibana Peel Extract, may be used.

In accordance with the various embodiments, one or more actives, alone or in combination, can be present in the composition from about 0.00001 to about 25 wt %, from about 0.00005 to about 15 wt %, from about 0.0001 to about 2 wt %, from about 0.05 to about 1 wt %, from about 0.02 to about 2 wt %, and from about 0.2 to about 1 wt %. In some embodiments, the composition comprises two, three, four or more actives having some, or all of which may be water soluble.

Thus, each one or combination of actives may be present by weight, based on the total weight of the composition, from about 0.00001, 0.00002, 0.00003, 0.00004, 0.00005, 0.00006, 0.00007, 0.00008, 0.00009, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, to about 25 percent, including increments and ranges therein and there between.

Solvent

In accordance with the disclosure, one more solvent is present in the composition. The solvent present in the cosmetic composition, according to the disclosure, includes, but is not limited to, denatured alcohol, propylene glycol, dipropylene glycol, butylene glycol, water and combinations thereof. In some embodiments, the solvent comprises water. Although these solvents are given as an example, it will be appreciated that other solvents compatible with cosmetic applications known in the art may be used.

In accordance with the various embodiments, solvent is present in the composition in an amount of from about 50 to about 99 wt %. In some embodiments, solvent is present in a given composition in an amount from about 70 to about 90 wt %, from about 75 to about 85 wt %, from about 80 to about 85 wt %, of from about 81 to about 84 wt %, of from about 82 to about 83 wt % or any suitable combination, sub-combination, range, or sub-range thereof. One of ordinary skill in the art, however, will appreciate that other ranges are within the scope of the invention.

Thus, the one or combination of solvents may be present by weight, based on the total weight of the composition, from about 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, to about 99 percent, including increments and ranges therein and there between.

Water

The compositions comprise from about 1 to about 99 wt % of water. The amount of water in the composition can range from about 1 to about 95 wt %; from about 50 to about 90 wt %; or from about 75 to about 85 wt %.

The pH of the composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Thickener

In some embodiments, the composition also comprises at least one thickener. The thickener may be mineral or organic in nature, and may comprise a particulate of any shape.

By way of non-limiting example, thickeners may be chosen from xanthan gum, cellulose gum, acacia senegal gum, guar gum, *sclerotium* gum, dehydroxanthan gum, gellan gum, agar, algin, talc, mica, silica, silica surface-treated with a hydrophobic agent, fumed silica, kaolin, polyamide (NYLON) powders (e.g. ORGASOL from Atochem), polyurethane powders, poly-β-alanine powder and polyethylene powder, powders of tetrafluoroethylene polymers (TEFLON), lauroyllysine, starch, boron nitride, hydrophobic silica aerogel particles, hollow polymer microspheres such as those of polyvinylidene chloride/acrylonitrile, for instance EXPANCEL (Nobel Industrie) or of acrylic acid copolymers (POLYTRAP from the company Dow Corning) and silicone resin microbeads (TOSPEARLS from Toshiba, for example), elastomeric polyorganosiloxane particles, precipitated calcium carbonate, magnesium carbonate, magnesium hydrogen carbonate, hydroxyapatite, hollow silica microspheres (SILICA BEADS from Maprecos), glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate, magnesium myristate and combinations thereof.

In some particular embodiments, the at least one thickener comprises xanthan gum. Optionally, mixtures of thickeners may be present in the compositions according to the disclosure. For example, a mixture of xanthan gum and *sclerotium* gum, may be used.

In accordance with some embodiments, at least one thickener may be present in the composition from about 0.1 to about 10 wt %, for example from about 0.1 to about 5 wt %, from about 0.1 to about 1 wt %, or from about 0.1 to about 0.2 wt %. In at least certain exemplary embodiments, the thickener is present in an amount less than about 1 wt %, such as less than about 0.5 wt %. In some other embodiments, the thickener is present in an amount up to about 10 wt %. It will be appreciated by one of skill in the art that the amount of thickener used will provide for lesser or greater thickening of the composition, thus enabling adjustment of thickness for a specific purpose. Thus, lesser amounts of thickener will be suitable for watery, toner type compositions, as represented in the instant examples.

Thus, the one or combination of thickeners may be present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, to about 10 percent, including increments and ranges therein and there between.

Optional Components

In some embodiments, there may be one or more additional optional components present in the cosmetic composition, according to the disclosure, selected from, preservatives such as phenoxyethanol, salicylic acid; penetrants; sequestrants; fragrances; chelating agents, such as EDTA; dispersants; opacifiers; film-forming agents; and combinations thereof. Although the aforementioned optional components are given as an example, it will be appreciated that other optional components compatible with cosmetic applications known in the art may be used.

In accordance with the various embodiments, the amount of optional components present in the composition can range from about 0 to about 50 wt %, from about 0.5 to about 30 wt %, from about 1.5 to about 20 wt %, and from about 5 to about 15 wt %. In some embodiments, one or more other optional components, alone or in combination, can be present in the composition according to the disclosure from about 0.05 to about 50 wt %, from about 0.05 to about 25 wt %, from about 0.1 to about 10 wt %, from about 0.25 to about 5 wt %, and from about 0.5 to about 3.5 wt %.

Thus, the one or combination of optional components may be present by weight, based on the total weight of the composition, from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45 to about 50 percent, including increments and ranges therein and there between.

The following Examples are provided for illustrative purposes only, and are not intended to be limiting.

EXAMPLES

Representative examples of inventive compositions are shown in Table 1.

TABLE 1

Inventive cosmetic composition examples:

| Phase | INCI US Name | % |
|---|---|---|
| A1 | WATER | 18.31 |
| A1 | DISODIUM EDTA | 0.05 |
| A1 | SALICYLIC ACID | 0.1 |
| A1 | PHENOXYETHANOL | 0.5 |
| A1 | DIPROPYLENE GLYCOL | 5 |
| A1 | BUTYLENE GLYCOL | 3 |
| A1 | METHYL GLUCETH-20 | 1.5 |
| A1 | HYDROXYPROPYL TETRAHYDROPYRANTRIOL | 0.5 |
| A1 | DIPOTASSIUM GLYCYRRHIZATE | 0.2 |
| A2 | GLYCERIN | 7 |
| A2 | XANTHAN GUM | 0.1 |
| B | PPG-6-DECYLTETRADECETH-30 | 0.2 |
| B | LAVANDULA ANGUSTIFOLIA (LAVENDER) OIL | 0.05 |
| C | WATER | 50 |
| D | WATER | 10 |
| D | 3-O-ETHYL ASCORBIC ACID | 1 |
| D | SODIUM CITRATE | 0.27 |
| D | CITRIC ACID | 0.18 |
| E | PAEONIA SUFFRUTICOSA ROOT EXTRACT | 0.01 |
| E | CITRUS AURANTIUM TACHIBANA PEEL EXTRACT | 0.01 |
| F | ALCOHOL DENAT. | 2 |
| G | CITRIC ACID | 0 |
| H | SYNTHETIC FLUORPHLOGOPITE (and) TITANIUM DIOXIDE | 0.02 |

Compositions and formulations as described in the representative embodiments herein are selected from commercially available materials, including, for example: Effect pigments, SUNSHINE SPECTRA line from Sun Chemical, Hydroxypropyl Tetrahydropyrantriol (40% water, 35% Hydroxypropyl Tetrahydropyrantriol, 25% propylene glycol).

Method

Effect pigments were selected and suspended in a toner formula (liquid cosmetic composition comprising at least one active) to ensure the compatibility of the "watery" composition and the pigments for the maximal effect. The use concentration for the effect pigment is in the range of 0.001 to 0.02 wt %. Such low concentration provides the most effective optical effect for the water-based liquid composition without having an appearance of a traditional makeup product.

By gently mixing the pigment into the liquid cosmetic composition (e.g. a leave-on skin toner), an iridescent optical effect is obtained for the formula. Further, the deposition of effect pigments on the skin for its users gives a desired "glowing" effect without the use of makeup products.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9-11 wt % and "about 2%" means 1.8-2.2 wt %).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1 to 10 wt %, such as 2 to 8 wt %, such as 3 to 5 wt %," is intended to encompass ranges of "1 to 8 wt %," "1 to 5 wt %," "2 to 10 wt %," and so on. All numbers, amounts, ranges, etc., are intended to be modified by the term "about," whether or not so expressly stated. Similarly, a range given of "about 1 to 10 wt %" is intended to have the term "about" modifying both the 1 and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A cosmetic composition comprising:
    a. pigment consisting of at least one effect pigment selected from the group consisting of i) at least one synthetic fluorphlogopite and ii) at least one synthetic fluorphlogopite and a metal oxide,
        wherein the total amount of pigment present in the composition is an amount that is not more than about 0.02%, by weight, based on the total weight of the composition;
    b. an emulsion comprising at least one oil and at least one surfactant;
    c. at least one active; and
    d. an aqueous carrier system comprising water, such that the cosmetic composition is water-based,
        wherein the composition is characterized as providing an instant and lasting glowing and brightening effect when applied to keratinous tissue; and
        wherein the pigment provides the instant and lasting glowing and brightening effect.

2. The composition of claim 1, wherein the pigment is present in an amount of from about 0.001 to 0.02%, by weight, based on the total weight of the composition.

3. The composition of claim 1, wherein the at least one oil present in the emulsion is employed in an amount of from about 0.01 to about 0.2% by weight, based on the weight of the composition.

4. The composition of claim 1, wherein the at least one surfactant present in the emulsion is employed in an amount of from about 0.1 to about 1.0% by weight, based on the weight of the composition.

5. The composition of claim 1, wherein the at least one active is present in an amount of from about 0.0001 to about 15% by weight, based on the weight of the composition.

6. The composition of claim 1, wherein the aqueous carrier system is present in an amount of from about 70 to about 85% by weight, based on the weight of the composition.

7. The composition of claim 1, wherein the metal oxide is selected from the group consisting of titanium oxide and iron oxide.

8. The composition of claim 1, wherein the at least one oil present in the emulsion is selected from the group consisting of *Lavandula angustifolia* (lavender) oil, *pelargonium graveolens* flower oil, *citrus aurantium* dulcin (orange) peel oil, *Rosmarinus officinalis* (rosemary) leaf oil, *menthe viridis* (spearmint) leaf oil, *citrus aurantifolia* (lime) oil, *melaleuca alternifolia* (tea tree) leaf oil, *citrus grandis* (grapefruit) peel oil, *citrus medica* limonum (lemon) peel oil, rose flower oil, *eucalyptus globulus* leaf oil, and combinations thereof.

9. The composition of claim 1, wherein the at least one surfactant present in the emulsion is selected from the group consisting of alkoxylated alcohols, PPG-6-Decyltetradeceth-30, PPG-26-BUTETH-26, CETETH-20, STEARETH-20, and combinations thereof.

10. The composition of claim 1, wherein the at least one active provides one or more benefits selected from the group consisting of brightening/whitening, improvement of skin tone, blemish control or reduction, reduction of redness, anti-aging, hydration, and combinations thereof.

11. The composition of claim 1, wherein the at least one active is selected from the group consisting of glycerin, glycol, methyl gluceth-20, hydroxypropyl tetrahydropyrantriol, tocopherol, 3-O-ethyl ascorbic acid, dipotassium glycyrrhizate and plant extracts, *Paeonia Suffruticosa* Root Extract, and *Citrus Aurantium* Tachibana Peel Extract, and combinations thereof.

12. The composition of claim 1, wherein the composition comprises a combination of three or more actives selected from the group consisting of (i) one or more of glycerin, glycol, methyl gluceth-20, hydroxypropyl tetrahydropyrantriol, tocopherol; (ii) one or more of dipotassium glycyrrhizate, 3-O-ethyl ascorbic acid; and (iii) one or more of plant extracts, *Paeonia Suffruticosa* Root Extract, and *Citrus Aurantium* Tachibana Peel Extract.

13. The composition of claim 1, wherein the aqueous carrier system further comprises at least one of denatured alcohol, propylene glycol, dipropylene glycol, butylene glycol, and combinations thereof.

14. The composition of claim 1, wherein the composition further comprises a thickener.

15. The composition of claim 14, wherein the thickener is present in an amount of from about 0.05 to about 0.5% by weight, based on the weight of the composition.

16. The composition of claim 15, wherein the thickener is selected from the group consisting of xanthan gum, cellulose gum, acacia senegal gum, guar gum, *sclerotium* gum, dehydroxanthan gum, gellan gum, agar, algin and combinations thereof.

17. A cosmetic composition comprising:
a. pigment consisting of at least one effect pigment selected from the group consisting of i) at least one synthetic fluorphlogopite and ii) at least one synthetic fluorphlogopite and a metal oxide,
wherein the total amount of pigment present in the composition is an amount that is not more than about 0.02%, by weight, based on the total weight of the composition;
b. an emulsion comprising at least one oil present in the emulsion is employed in an amount of from about 0.01 to about 0.2% by weight, based on the weight of the composition and at least one surfactant present in the emulsion is employed in an amount of from about 0.1 to about 1.0% by weight, based on the weight of the composition;
c. at least one active present in an amount of from about 0.0001 to about 15% by weight, based on the weight of the composition; and
d. an aqueous carrier system comprising water, such that the cosmetic composition is water-based,
wherein the composition is characterized as providing an instant and lasting glowing and brightening effect when applied to keratinous tissue; and
wherein the pigment provides the instant and lasting glowing and brightening effect.

18. The composition of claim 17, wherein the metal oxide is selected from the group consisting of titanium dioxide and iron oxide.

19. The composition of claim 17, wherein the at least one oil present in the emulsion comprises *Lavandula Angustifolia* (Lavender) Oil.

20. The composition of claim 17, wherein the at least one surfactant present in the emulsion comprises PPG-6-Decyltetradeceth-30.

21. The composition of claim 17, wherein the at least one active comprises (i) one or more of glycerin, glycol, methyl gluceth-20, hydroxypropyl tetrahydropyrantriol, and tocopherol; (ii) one or more of sodium citrate, citric acid, 3-O-ethyl ascorbic acid; and (iii) one or more of plant extracts, *Paeonia Suffruticosa* Root Extract, and *Citrus Aurantium* Tachibana Peel Extract.

22. The composition of claim 17, further comprising a thickener present in an amount of from about 0.5 to about 2.5%, by weight, based on the weight of the composition.

23. The composition of claim 22, wherein the at least one thickener comprises xanthan gum.

24. The composition of claim 17, wherein the aqueous carrier system further comprises one of denatured alcohol, propylene glycol, dipropylene glycol, butylene glycol, and combinations thereof.

25. The composition of claim 17, further comprising one or more additional components selected from the group consisting of preservatives; penetrants; sequestrants; fragrances; chelating agents; dispersants; film-forming agents; thickener and combinations thereof.

26. The composition of claim 25, wherein each of the one or more additional components is present in the composition in an amount, by weight, from about 0.5 to about 15% by weight, based on the total weight of the composition.

* * * * *